(12) United States Patent
Egydio

(10) Patent No.: US 7,931,583 B2
(45) Date of Patent: Apr. 26, 2011

(54) SURGICAL METHOD AND AUXILIARY DEVICE TO CORRECT PENIS CURVATURE

(76) Inventor: Paulo H. Egydio, Sao Paulo (BR)

( * ) Notice: Subject to any disclaimer, the term of this patent is extended or adjusted under 35 U.S.C. 154(b) by 0 days.

(21) Appl. No.: 12/817,905

(22) Filed: Jun. 17, 2010

(65) Prior Publication Data

US 2010/0256444 A1   Oct. 7, 2010

Related U.S. Application Data

(62) Division of application No. 10/550,810, filed as application No. PCT/BR03/00050 on Mar. 31, 2003, now Pat. No. 7,780,591.

(51) Int. Cl.
*A61B 19/00* (2006.01)
(52) U.S. Cl. .......................................... 600/40; 128/898
(58) Field of Classification Search ............... 600/38–41; 128/897–898
See application file for complete search history.

(56) References Cited

U.S. PATENT DOCUMENTS

| | | | |
|---|---|---|---|
| 6,582,356 B2* | 6/2003 | Kim | 600/40 |
| 7,637,862 B2* | 12/2009 | Moore | 600/40 |
| 2010/0130816 A1* | 5/2010 | Gekhter | 600/39 |
| 2010/0204543 A1* | 8/2010 | Sanchez Martinez | 600/39 |

* cited by examiner

*Primary Examiner* — John P Lacyk
(74) *Attorney, Agent, or Firm* — David A. Guerra

(57) ABSTRACT

The invention refers to a device for correcting penis curvature. The device includes at least two first rules linked together by a junction and adjustable therebetween along a hypothetical plan containing the first rules, which has rotation and translation between the first rules. A flexible measurement element is connected to the junction of the first rules. At least two second rules each of which being respectively fixed to one of the first rules, and perpendicularly to the first rules. The second rules are able to move in translation along the second rules lengths. The first rules permit a determination of a central penis axis and tangential lines on a penis. The second rules are used in a determination of perpendicular lines on the penis.

19 Claims, 4 Drawing Sheets

SURGICAL METHOD AND AUXILIARY DEVICE TO CORRECT PENIS CURVATURE

CROSS-REFERENCE TO RELATED APPLICATIONS

This application is a divisional application under 35 U.S.C. §121 and 37 CFR 1.53(b) based upon co-pending U.S. application Ser. No. 10/550,810 filed Sep. 23, 2005. Additionally, this divisional application claims the benefit of priority of co-pending U.S. application Ser. No. 10/550,810 filed Sep. 23, 2005, and International Application No. PCT/BR2003/000050 filed Mar. 31, 2003. The entire disclosures of the prior applications are incorporated herein by reference.

BACKGROUND OF THE INVENTION

1. Field of the Invention

The invention refers to a surgical method, as well as a method determine the location of the main incision line, method determine the geometrical distribution and size of forked ends of the main incision line and a method determine the defect dimensions, being all methods geometrical and auxiliary for a surgical intervention to correct penis curvature. Furthermore, the invention also refers to an auxiliary device to the various methods.

More specifically, the invention refers to a surgical method with the purpose to correct penis curvature, being it inborn or acquired as in Peyronie's disease, and additional methods used during said surgery, as follows:

- to accurately determining the location of the main incision line;
- determine the distribution and size of the main incision line's forked ends; and
- determine the dimensions of the defect to which a graft will be applied; as well as an auxiliary device to said methods.

2. Description of the Prior Art

Irregular penis curvature while erected may be inborn or of acquired origin. In the latter case, it is called Peyronie's disease, as a reference to the French physician who discovered it.

Penis structure is formed by a tissue recovering the corpora cavernosa called tunica albuginea. On the other hand, elastic fibers integrating the tunica albuginea form an irregular framework on which collagenous fibers lie. These two structural components are essential to penis configuration during erection, as they allow the increase of penis diameter and extension during tumescence. Any defect on collagenous and resilient fibers of the tunica albuginea can lead to significant changes in erection hemodynamics. Erection hemodynamics means, in this application, the movement with which blood runs around the corpora cavernosa in the penis erection process.

The tunica albuginea performs an essential role in erection due to its flexibility and stiffness characteristics. The Penis maximum length, width and curvature while in erection are determined by the configuration of the tunica albuginea.

In case of an inborn curved penis, the problem is caused by lack of flexibility of the tunica albuginea and/or its covers. On the other hand, Peyronie's disease is characterized by developing cicatricial tissue on said tunica albuginea, reducing its flexibility.

During erection, the normal side of the penis, the flexibility of which is preserved, presents the usual gain in size, while the affected size, due to a loss in flexibility of the tunica albuginea and/or its covering, does not expand equally, with a consequent curvature towards the same size and loss of penis functional size.

Not only the functional size of the penis is reduced but also, in more severe cases, sexual act practice by man is hindered, keeping him from having a normal life.

Currently existing techniques to correct penis curvature basically consist of (1) reducing the long side of the penis to the size of the short side, or (2) increase the short side of the penis to the same size of the long side.

When the reduction of the long side of the penis to the size of the short side is desired, the following is done: (1) elliptical excision on the tunica albuginea on the opposed side of the penis to that one with the defect, subsequently suturing borders; (2) plication or pleat of the tunica albuginea on the opposed side to that one with the defect, to reduce the long side not resorting, however, to an incision or resection of the tunica albuginea; or (3) lengthwise incision on the longer side followed by crosswise suture.

Said techniques incur a few disadvantages. Firstly, while reducing the long side to the size of the short side, curvature can be corrected, but the patient will be dissatisfied with the reduction of the size of the penis, which will be as extensive as the existing curvature. Therefore, patients are reluctant to accept this kind of surgical procedure. Another disadvantage consists in the fact that the application of said skills do not include an exact determination of the excision place and the size of the ellipse to be taken off or the place and size of lengthwise plication(s), or incision(s) and crosswise suture.

As previously shown, other skills extend the short size of the penis to the same size of the long side. These surgical procedures are made by incision and/or excision of the tunica albuginea by making use of grafts to cover the side which will become longer after being submitted to surgery.

Procedures to extend the short side of the penis overcome the disadvantage of reducing the size of the penis, but incur in other problems as described below.

In about 70% of Peyronie's disease cases, the plaque of cicatricial tissue is palpable. At the time of the surgery, the surgeon can feel the plaque of cicatricial tissue and determining the place where incision or excision will be made. In 30% of cases, there is no palpable cicatricial tissue during surgery. It is possible that the tunica albuginea is less flexible without alteration of it thickness so as not to be palpable, and it is also known that there are flexibility changes in the tunica farther from the plaque, thus explaining cases in which the substitution of plaque(s) do not correct penis deformation. Furthermore, there are patients presenting multifocus plaques.

Due to the above, surgeries based on cicatricial tissue plaques do not solve all cases and may not correct penis curvature with its single removal, since the flexibility of the tunica is compromised at a distance of the plaque(s).

Therefore, the procedure of excision of plaque(s) by itself may not be sufficient to correct penis curvature, and complementary relaxation incisions must be added.

Since the patient's main claim is the penis deformation (and not the plaque, when present), it is possible to correct it with the single incision or relaxation incisions (correction by expansion, instead of substitution). By means of a linear incision, it is possible to create a simpler defect on the tunica albuginea, which will be covered by a graft, facilitating the suture procedure.

Another disadvantage of the excision and graft procedures is the high rate of post-surgery erectile dysfunction which, in various studies of the state of the art, are reported as varying between 12% and 100% (Dalkin, B. L.; Carter, M. F., *Veno-* genic Impotence following dermal graft repair for Peyronie's disease, J. Urol., v. 146 (3), p. 849-51, 1991).

Currently, no matter the method to correct penis curvature, more accurate methods to determine the correction are not employed.

When the increase of the short side of the penis is desired with consequent graft application, there is also no accurate procedure to determine the dimensions of said defect of the tunica and the corresponding graft. Techniques measure the defect on the tunica with the penis in a flaccid state, under traction, which is not coincident with the defect required to correct the deformity, which is related to the stretched tunica during erection.

Furthermore, for all previously shown surgical skills, it is necessary to keep the penis erect to visualize and determining the location of the incision line, even if there is no accurate method for that. Currently, erection is forced by continuous saline solution injection within the corpora cavernosa. This injection is made by means of two needle syringes containing saline solution applied within corpora cavernosa. The problem to effect said practice is the need for the assistants to make the injection and, since there is much saline solution leakage, the syringe needs to be changed to fill it again with saline solution. Therefore, the penis will again become flaccid and a new erection will have to be induced determine incision locations. According to one of the alternatives of the invention, the use of an infusion pump allows a stable erection under maximum rigidity, providing a surgery with optimized results.

SUMMARY OF THE INVENTION

The invention aims to solve the problems as found in the prior art.

More specifically, an object of the invention is a surgical method to correct penis curvature.

Furthermore, another object of the invention is a geometrical method to accurately determining the most appropriate location of the main incision line to be made in a surgery to correct penis curvature.

Another object of the invention is a geometrical method to accurately determining distribution and the size of the forked ends of the main incision line to be made in a surgery to correct penis curvature.

Another object of the invention is a geometrical method to accurately determining the dimensions of the defect created by the surgery to correct penis curvature when the shorter side of the penis should be extended, aiming at introducing a graft.

One further object of the invention is an auxiliary device to the surgery to correct penis curvature based on the geometrical methods of the invention.

To solve deficiencies found in the prior art, we have developed a surgical method to correct penis curvature, geometrical methods (1) to accurately determining the location of the main incision line, (2) determine the distribution and size of the forked ends of said incision, as well as (3) determine the dimensions of the defect created on the tunica during a surgery to correct penis curvature, due to the introduction of graft. The invention also refers to an auxiliary device to realize its methods.

In a first aspect, the invention deals with a method to accurately determining the location of the main incision line in a surgery to correct penis curvature, which comprises the following steps:
  a. inducing and keeping the penis erect;
  b. determining a line along the central penis axis;
  c. determining a tangential line to each one of the two substantially straight segments adjacent to the penis curvature to be corrected;
  d. determining the bisectrix on the intersection of said two tangential lines; and
  e. determining the main incision line, whose direction coincides with the bisectrix direction.

It is important to mention that the invention does not involve the usual surgical practice regarding e.g. incisions themselves, patient's anesthesia, adaptation or asepsis of the surgical environment, appropriate surgical instruments, etc. These are aspects which the one skilled in the art is entitled to apply as conveniently as possible.

The method of the invention, in a first alternative, consists firstly of inducing and keeping penile erection. Erection may be induced by saline solution injection under pressure within the penis' corpora cavernosa.

In a particular embodiment of the invention, a pump is used, particularly an infusion pump, for continuous saline solution injection. This avoids the handling of syringes and variation in saline solution supply, allowing the penis to remain erect as appropriately as possible to best make the surgery, i.e. under continuous maximum erection, during the whole time required to apply the method.

After the erection is obtained, a line is determined and optionally drafted in coincidence with the central penis axis, following its curvature. The central line is drafted over the imaginary plan (referred to below as working plan) containing both substantially straight segments of the penis adjacent to the curvature to be corrected, i.e. a first segment before the curve and a second segment after the curve.

The following path consists in determining tangential lines to both said straight segments over the working plan. In case there is one single curvature to be corrected by surgery, a tangential line to the first segment is drafted from the base of the penis towards the glans; another tangential line to the second segment is drafted, starting from the glans towards the base. Said tangential lines may be drafted with reference to the central penis axis or with reference to the higher and lower lines, limiting the lateral penis surfaces over the working plan.

The intersection point of both tangential lines giving origin to the bisectrix line formed between both tangents determining the maximum penis curvature region. A crosswise line around the penis body or tunica albuginea is determined by following the bisectrix line direction. Said line is circumferential to the penis body, indicating the direction of the main incision. The extension of the main incision line optionally does not intercept both insertions of the intercavernosum septum, not excluding, however, any other configuration.

Within this first aspect of the invention, the bisectrix line determining in a substantially accurate way the direction of the main incision, since this is the most appropriate region to correct the defect causing penis curvature. Guided by that line, the physician makes a main incision partially surrounding the penis body, long enough to break force lines present in the curvature, e.g. in case of increasing the shorter side of the penis. "To break force lines", as used herein, means to eliminate tensions favoring or tending to allow the curvature to be corrected to remain.

In a second aspect, the invention deals with a method determine the geometrical distribution and size of the terminals in a V-incision on each one of the ends of the main incision line in a surgery to correct penis curvature. From a surgical point of view, it is not only important determine in a substantially accurate way the location of the main incision line to be assured that the defect is being corrected as appropriately as possible, but it is also required that the distribution and size of forked ends on the ends of the main incision line are appropriately determined for the graft anchoring over the generated defect to be efficient, defect and graft having simpler configurations, thus facilitating the suture procedure.

It is not an object of the invention determine which is the best format to be used for said incision, but to provide means determine the geometrical distribution and size of the V-incision to effectively help to correct penis curvature. The method of the invention assumes that the main incision line surrounding the patient's penis as an incomplete circumference, following the orientation of the previously determined bisectrix line, has already been drafted or the guiding incision has also been made by the surgeon (preferably not reaching corpora cavernosa to avoid loss of erection, by way of leakage of saline solution).

The invention therefore also deals with a method determine the geometrical distribution and dimension of forked ends of an incision, of an angle $\alpha$ between said terminals, in a surgery to correct penis curvature, comprising the following steps, which are additional and subsequent to those of the already described method determine the location of the main incision line:

f. determining two perpendicular lines respectively to said tangential lines, not crossing the penis curvature region; each one of them preferably crosses said perpendicular line in one point where said tangential lines to the central penis axis start to separate from it;

g. determining the difference (C) between the extension of the longer side and the extension of the shorter side of the penis, between said perpendicular lines, over the working plan;

h. determining a line which is perpendicular to the main incision line, crossing it at a point (G), as large as said difference (C), of ends (F) and (F'), equally distant from the bisectrix;

i. determining the dimension of a segment (S), so that:

$$S = tg(90-\alpha/2) \cdot C/2$$

in which $\alpha$ is the desired angle between both ends on the fork of the main incision line and (C) is the previously mentioned difference.

j. determining the location of a point (E), distant from the point (G) the value of extension of said segment (S) along the main incision line;

k. link the point E to the points (F) and (F'), so to obtain the distribution of forking ends under the desired geometry, with a size determined by the distance between points (E) and (F), or (E) and (F').

The end point (G) of the main incision line as described above is opposed to an end point (G') on the opposed end of the same line. Forked ends may therefore be made as described above on each one of the ends of the main incision line.

Perpendicular lines as mentioned on step (f) above may be drafted by passing through any point of the central penis axis which do not lie on the penis curvature region since, no matter which is its location, they allow to detect the dimensional difference between both sides of the curved penis, one longer and another shorter one. Particularly, said perpendicular lines can be drafted as equally distant from the bisectrix, not excluding any other option.

After the perpendicular lines to the tangential lines are drafted, the extension of C is determined between both curved segments composing the longer and shorter lateral lines of the penis body or the tunica albuginea, over the working plan. The length difference between these two segments substantially corresponds to the size difference between the longer and shorter sides of the penis, substantially determining the required distribution and size of required and enough incisions for the forked ends of the main incision, generating a controlled defect in the surgery to increase the shorter side of the penis.

The difference (C) is used for the corrective surgery to reduce the longer side of the penis, by subtracting said extension (C) from the dimension of the longer side of the penis. The reduction can be made by means of (1) plication or pleat and/or (2) excision and suture, and/or (3) lengthwise incision and crosswise suture. Said procedures, alone or combined among them in any way, may be applied to one single region over the curvature region or to more than one region over the curvature region, as long as the dimension (C) corresponds to the total extension to be reduced.

The method can be employed for any angle $\alpha$ of the V-incision, advantageously between 60° and 180°, particularly between 90° and 150° and, most particularly, about 120°.

One further aspect of the invention consists of a method to determine the dimensions of a defect to be filled in by a graft, when the elongation of the short side of the penis is desired for a surgery to correct its curvature. To obtain a rectangular defect, the method basically comprises the steps of:

a. determining the extension of the main incision line between points (E) and (E'), as per the step (j) of the process as described further above, and the distance between point (G) and (G') representing the length (L) of said defect outside any constructive area;

b. determining the difference (C) between the extension of the longer side and the extension of the shorter side of the penis, between said perpendicular lines, over the working plan; as per the step (g) of the method as described further above, representing the width of said defect.

The method can optionally comprise the following additional steps:

c. proportionally increasing, if necessary, the length L and width (C) measurements of the defect, from the steps (a) and (b) above, if the grafting material to be used presents contraction;

d. transporting and drafting the length and width measurements of the defect, from the steps (a) and (b) above, with the optional correction of (c) over the grafting material (e.g. bovine pericardium or dermis).

In the method determine the dimensions of the rectangular defect, between end points (F-F') and (F"-F"') of the main incision line are optionally located in the region of the longer side of the curved penis, but not excluding any other embodiment.

To obtain a trapezoidal defect which is appropriate for lateral correction cases, or a predominantly lateral curvature, the method basically comprises the following steps:

a. determining the extension of the main incision line between the end points (E) and (E'), as per the step (j) of the process as described further above and the distance between points (G) and (G'), representing the length (L) of said defect;

b. determining the difference (C) between the extension of the longer side and the extension of the shorter side of the penis, between said perpendicular lines, over the working plan; as per the step (g) of the process as described further above;

c. determining the dimension of the shorter base D of the trapezium between about 10% and about 50% of the (C) value;

d. determining the dimension of the longer base of the trapezium between about 110% and about 150% of the (C) value. C and D are typically summed up.

The method can optionally comprise the following additional steps:

e. proportionally increasing, if necessary, the measurements from the steps (a), (c) and (d) above if the grafting material to be used presents contraction;

f. transporting the measurements from steps (a), (c) and (d), respectively defining height, longer base and shorter base of the trapezoidal shape of the generated defect, with the optional correction of step (e) over the grafting material.

In the method determine the dimensions of the trapezoidal defect, between end points (F-F') and (F"-F"') of the main incision line are particularly located so that its path does not cross both insertions of the intracavernosum septum.

In one more aspect, the invention deals with a surgical method to correct penis curvature, which comprises the following steps:

a—geometrically determining the location of the main incision line crosswise to the central penis axis, so that it is located over the maximum curved region to be corrected.

b—to correct the curvature by increasing the shorter side of the penis:

b1—geometrically determining the desired distribution and size of the forked ends of the main incision line;

b2—geometrically determining the size of the defect created by the incision on the main line and the forked ends;

b3—effecting the main incision and the incision of the forked ends, generating a defect;

b4—implant the graft over said defect, substantially coincident with the defect, optionally with corrected dimensions, bearing in mind the contraction of the grafting material;

c—to correct the curvature by reducing the longer side of the penis, the longer side is reduced in the curvature region by means of one or more of the following skills as applied over one or more places within the curvature region:

c1—plication or pleat; and/or c2—excision and suture; and/or c3—lengthwise incision and crosswise suture.

In its various aspects, the invention is also applied to surgeries to correct penis curvature by reducing the longer side of the penis, or even when it is chosen to simultaneously partially reduce the longer side of the penis and partially increase the shorter side of the penis.

In one more aspect, the invention deals with a device developed to help the realization of the above described methods.

Said device comprises:

a. two longer rules linked together by a junction and adjustable between them along a hypothetical plan containing them, having rotation and/or translation between one and the other;

b. a flexible measurement element connected to said junction of the two longer rules;

c. two shorter rules, each one respectively fixed to one of said longer rules, perpendicularly to them, which are able to move in translation along their lengths.

d. optionally, elements to non-permanently clamp the device to the penis or to portions of it—e.g. clamps or staples.

e. a second optional device comprising the above elements, associated to the first device and substantially parallel to it.

Both longer rules are associated by any appropriate means of junction, such as a fixing pin allowing a rule to both rotate with relation to the other and also to run alongside the other, e.g. by means of rails associated to them. Due to this characteristic, both longer rules can assume any position with relation to each other, along a hypothetical plan containing them.

Optionally, the device is provided with a clamping element allowing to non-permanently fix the position of one rule regarding the other.

Associated to said junction, e.g. a fixing pin, there is also a flexible measurement element, such as a flexible ribbon with measuring marks which can rotate over the same plan of said both longer rules. In a particular embodiment of the invention, the fixing pin comprises two concentric axes. One of them is fixed to one of the longer rules and the other one is fixed to the measurement ribbon. On each concentric axis, there is a mark similar to a protractor, in which one can easily visualize e.g. (1) the angle between the rule and the measurement ribbon and therefore determining the average angle between both rules, and (2) the angle between both measurement rules, so determine the curvature grade to be surgically corrected.

The device also comprises two shorter rules, each one fixed to one of said longer rules. The shorter rules stay in perpendicular position to longer rules, are optionally flexible and can run along the length of said longer rules, e.g. by means of the same rails of longer rules.

With the help of the device, it is possible to employ the invention to determine in a substantially accurate way the location of the main incision line, distribution and size of its forked ends, and defect and graft dimensions.

With the help of the longer rules, tangential lines to the central penis axis line are located or drafted. The central penis line can optionally also be drafted, if interesting for visualization. Drawing of tangential lines can be made at any point of penis straight segments, as long as over the working plan. This means that one can draw perpendicular lines on both the lower side of the penis and on the middle of its body, or even on the higher side of the penis, since the determination of the bisectrix is independent from the horizontal position of the device.

By putting the device closer to the penis, one can attach a rule to the penis to draw the first tangential line. The other rule is adjusted to the working plan to draw the second tangential line, eventually also attaching it to the penis. Tangential lines can be drawn according to rule orientation, by any appropriate means, be it a pen, a toothpick dipped into methylene blue or any other.

After tangential lines are drawn, the bisectrix line is drawn with the help of the central measurement ribbon. The central measurement ribbon is adjusted so to remain in an average angle between both longer rules—e.g. by means of the central pin as already mentioned, provided with two concentric axes with marks allowing the determination of the mean angle between both longer rules, which determines the bisectrix of intersection of both rules.

Since the measurement ribbon is flexible, it can be bent over the body of the penis. In a preferred embodiment of the invention, the measurement ribbon has a central tear through which it is possible to draw with appropriate accuracy the bisectrix line around the penis. Particularly, the central tear is between 1 mm and 5 mm wide.

With the help of the two shorter rules, it is possible to draw perpendicular lines to the tangential lines, determine the difference in size between the longer and shorter sides of the penis along the working plan. It is possible to put the shorter rules nearer or farther from the bisectrix, visually verifying its location with relation to the regions where penis curvature begins. The shorter rules may be flexible and surround the body of the penis and optionally serve as a guide to draw such lines around the whole penis.

It is also possible to use two such devices in parallel, associated in any way known by the one skilled in the art, in support to the methods of the invention.

All rules and component parts of the auxiliary device of the invention can contain measurement marks, such as millimeter marks or guiding marks for angles. Particularly, the device is disposable.

The auxiliary device of the invention can be of any material, such as metal, polymers, composites, etc. In a preferential embodiment, the metal is a stainless steel alloy 18Cr-8Ni.

The device of the invention is auxiliary to the method determine the main incision line, to the method determine the distribution and size of the forked ends of the main incision line, to the method determine dimensions of the defect as generated by the surgery to correct penis curvature and its corresponding graft, and the surgical method to correct penis curvature, both to increase the short side and to reduce the long side of the penis.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The objects, improvements and effects of the methods and device of the invention will be better understood from the description presented below, with reference to the attached figures, given only as an illustration of a particular embodiment of the invention. Said figures are schematic, with dimensions or proportions which may not correspond to reality, since they only aim to didactically illustrate the invention, not imposing any limitations to its scope other than those included in the claims further below.

The same reference numerals refer to the same parts throughout the various figures.

DESCRIPTION OF THE PREFERRED EMBODIMENT

Figure 1:
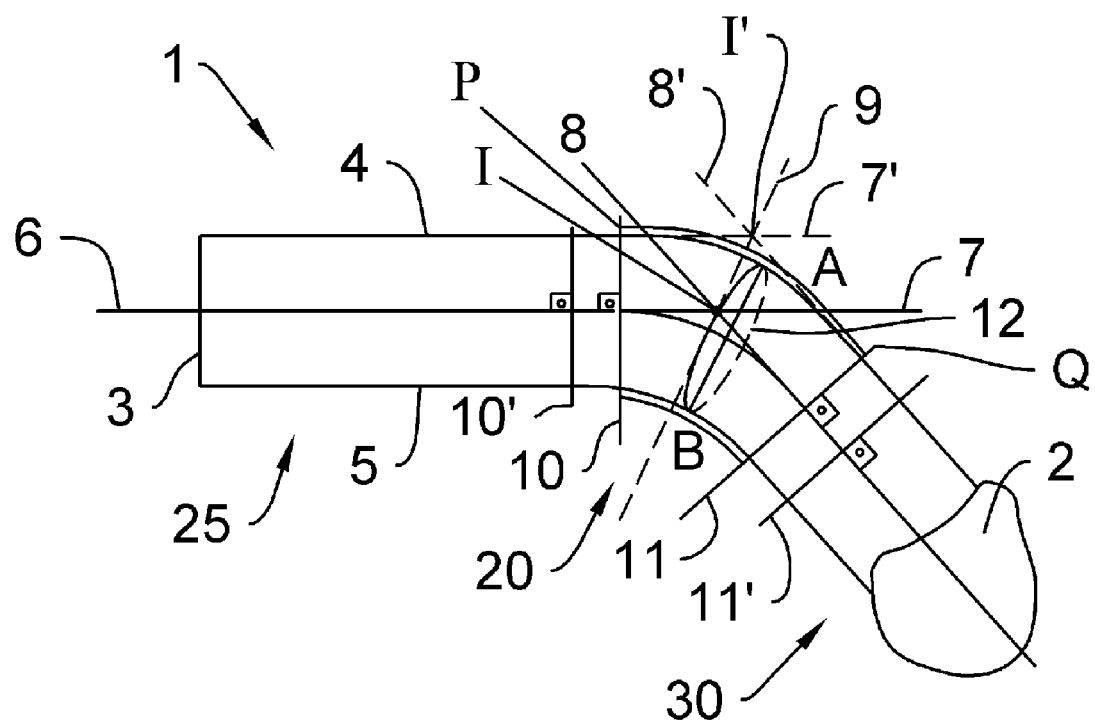
FIG. 1 is a representation of a penis having curvature to be surgically corrected.

FIG. 1 shows a penis (1) provided with ventral curvature (20), located between two substantially straight segments (25) and (30). The segment (25) starts at the base (3) of the penis (1) and the segment (30) ends at the glans (2). The working plan is the plan containing segments (25) and (30), i.e. as seen by an observer looking at FIG. 1 on the sheet of paper.

A first aspect of the invention refers to a method to accurately determine the location of the main incision line in a surgery to correct penis curvature. The several steps of this method will be detailed below with reference to the figures:

a. inducing and keeping the penis erect—an infusion pump, not shown, is used to obtain maximum erection of the penis (1);

b. determining a line along the central axis of the penis—this is line (6).

c. determining a tangential line to each one of the two substantially straight segments adjacent to the curvature (20)—these are lines (7) and (8), respectively tangential to the straight segments (25) and (30) crossing at the point (I). Said tangential lines can be determined at any point along the width of the penis over the working plan, e.g. as shown by lines (7') and (8') which are crossed at the point (I').

d. determining the bisectrix at the intersection of said both tangential lines—this is line (9), which is at the average angle between both tangents (7) and (8), or (7') and (8'), including the point (I) or (I').

e. determining the main incision line, whose direction coincides with the bisectrix direction—the circumference line (12) shows the direction of the main incision on FIG. 1.

The surgeon can draw all lines mentioned in the method, or how many he or she wishes, since they only serve as a support for the accurate determination of the main incision line.

Figure 3:
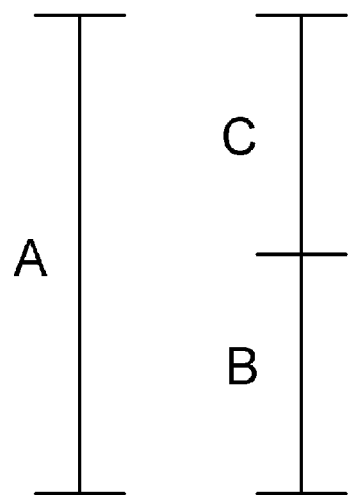
FIG. 3 is a schematic representation of the geometrical relations obtained from the method of the invention.

Another particular aspect of the invention is a method to accurately determine the geometrical distribution and size of the forked ends of said main incision line, comprising steps (a) to (e) of the described method and, including the following steps:

f. determining two perpendicular lines (10) and (11) respectively to said tangential lines (7) and (8), or (7') and (8')—see FIG. 1. Lines (10) and (11) pass respectively through points (P) and (Q), which are the nearest points to the curvature (20), i.e. they pass through the points where tangential lines (7') and (8') start to separate from lines (4) of the penis (1) surface, no longer coinciding with them. Corresponding points are determined when tangents (7) and (8) get farther from the central penis axis (6). Other pairs of perpendicular lines such as (10') and (11'), farther from the curvature (20), are perfectly acceptable, as well as (10) and (11'), or (10') and (11), as long as they are taken and kept as standards for the following step.

g. determining the difference (C) (concerning the curvature (20)) between the extension (A) of the longer side and the extension (B) of the shorter side of the penis, between said perpendicular lines (10) and (11), over the working plan, as seen on FIG. 1. The difference (C) can be visually obtained as shown on FIG. 3. As stated, if the adopted perpendicular lines were e.g. (10') and (11'), the difference (C) would be calculated by taking the extension from the longer side between lines (10') and (11') and mandatorily the extension of the shorter side would also be measured between lines (10') and (11').

h. determining a perpendicular line to the main incision line, crossing it at a point (G), with the same length of said difference (C), with ends (F) and (F'), equally distant from the bisectrix 9—this means to determine a line (15) crosswise to the main incision line (12), passing through the point (G) (or (G') at the opposed end) with length equal to said difference (C), with ends (F) and (F') (or (F''') and (F'''')) at the opposed end) equally distant from the point (G) (or (G')) of the main incision line (12). Therefore, on line (15), the distance between (F) and (G) is equal to the distance between (F') and (G), and is equal to (C)/2;

i. determining the dimension of a segment (S), so that $S = \mathrm{tg}(90 - (\alpha/2)) \cdot C/2$ in which $\alpha$ is the desired angle between both ends on the fork at the end ((E) or (E')) of the main incision line (12) and (C) is the previously mentioned difference.

j. Determining the location of a point (E) (or (E') at the opposed end), distant from the point (G) (or the point (G') at the opposed end), with the value of extension of said segment (S) along the main incision line (12).

k. link the point (E) to the points (F) and (F'), so as to obtain the distribution of the ends (14) and (14') of the fork under the desired geometry, i.e. with an angle α between the ends (14) and (14') with a size determined by the distance between points (E) and (F), or (E) and (F') (or even (E')-(F''') or (E')-(F''''), at the opposed end of line (12)).

Particularly, points (E) and (E') of the main incision line (12) are located on the longer side (4) or with longer curvature (20) of the penis.

The determination of the length of the segment (S) is based on trigonometry. We can see on FIG. 2 that, in the triangle formed by the sides (14), (S) and segment F-G of line (15):

the sum of the internal angles of the triangle is $\beta+\alpha/2+90=180$, therefore $\beta=90-\alpha/2$;

the tangent to the angle β is equal to the ratio between (S) and (C)/2 dimensions (opposed cathetus to adjacent cathetus).

Joining these two equations and isolating (S), we reach:

$S=tg(90-(\alpha/2)\cdot C/2$

By way of a typical embodiment, adopting α=120°, (S) will be equal to C/4.

Figure 4:
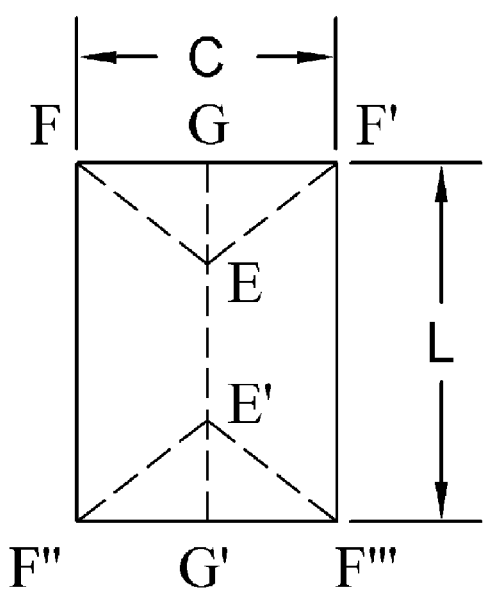
FIG. 4 is a schematic representation of a graft with rectangular shape.

One further aspect of the invention consists of a method determine the dimensions of a defect to be filled in by a graft, when the elongation of the short side of the penis is desired for the surgery to correct curvature. To obtain a rectangular defect, the method basically comprises the steps of:

a. determining the extension of the main incision line (12) between points (E) and (E') and the distance between points (G) and (G'), representing the length (L) of said defect, as shown on FIG. 4.

b. determining the difference (C) between the extension (A) of the longer side and the extension (B) of the shorter side of the penis, between said perpendicular lines ((10) and (11)), over the working plan; with the difference (C) representing the width of said defect, as shown on FIG. 4 Check if the vertexes of the defect are the points (F), (F'), (F''), (F''').

c. proportionally increase, be it the case, the length and width measurements of the defect, from the steps (a) and (b) above, with the graft material to be used if it presents contraction, e.g. bovine pericardium is not subject to substantial contraction, as opposed to dermis.

d. transporting and drafting the length and width measurements of the defect, from the steps (a) and (b) above, with the optional correction of item (c) over the graft material.

Figure 5:
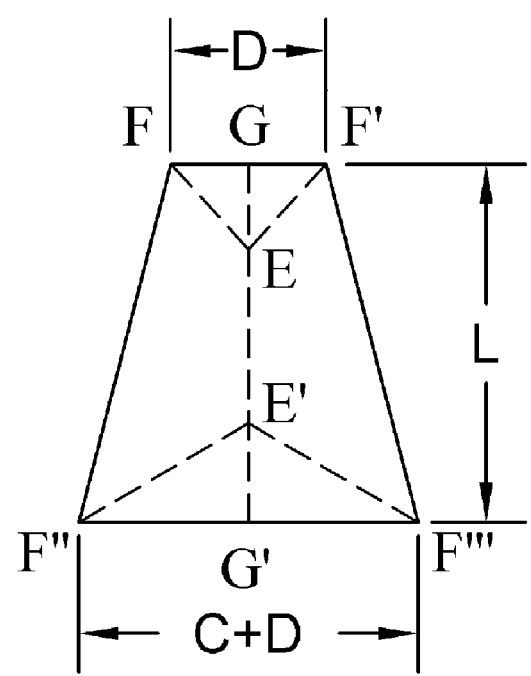
FIG. 5 is a schematic representation of a graft with trapezoidal shape.

To obtain a trapezoidal defect which is appropriate for lateral correction cases, or with predominantly lateral curvature, the method basically comprises the steps (a) and (b) above, along with the following:

c. determining the dimension of the shorter base of the trapezium between about 10% and about 50% of the value (C) a value (X), obtaining the dimension (D), from FIG. 5.

d. to obtain the dimension of the longer base of the trapezium, (C) is summed to (D), see FIG. 5.

e. proportionally increasing, be it the case, the measurements from steps (a), (c) and (d) above if the graft material to be used is contracted;

f. transport the measurements from steps (a), (c) and (d), respectively defining height, shorter base and longer base of the trapezoidal shape of the generated defect, with the optional correction of step (e) over the graft material.

In the cases of creation of a defect for lateral or predominantly lateral curvatures, the distribution and dimensions of the forked ends are proportionally changed, bearing in mind the trigonometric relation and applied on items (i), (j) and (k) of the method as described further back.

Figure 6:
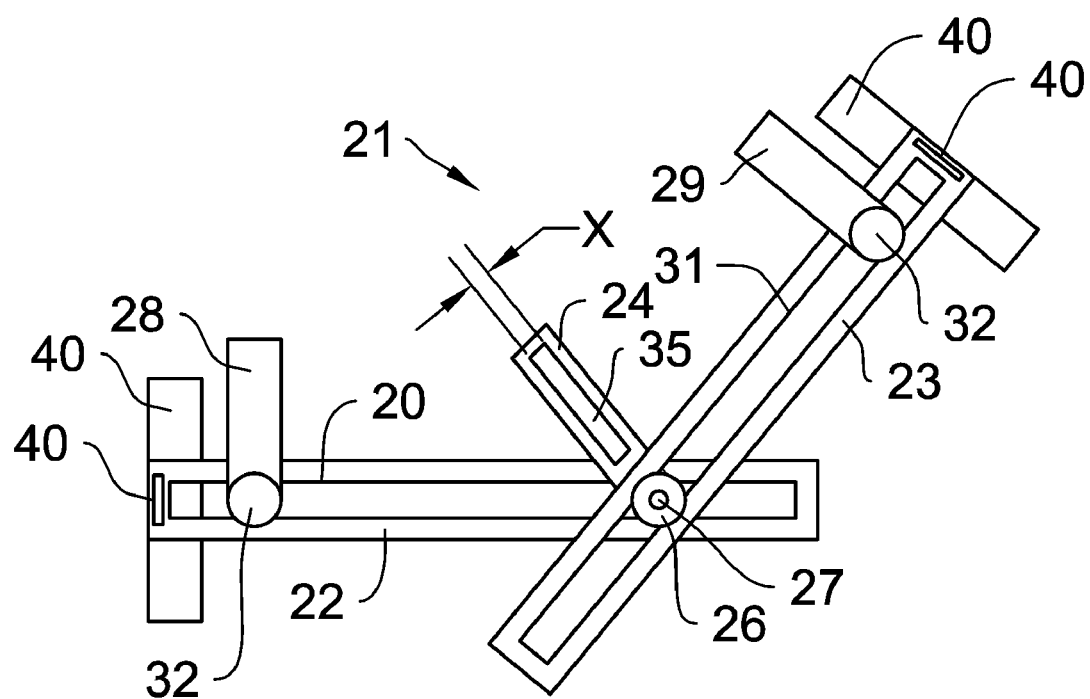
FIG. 6 is a representation of the auxiliary device to the methods of the invention.

In FIG. 6, one more aspect of the invention is illustrated, i.e. an auxiliary device (21) to the realization of the above described methods.

Figure 2:
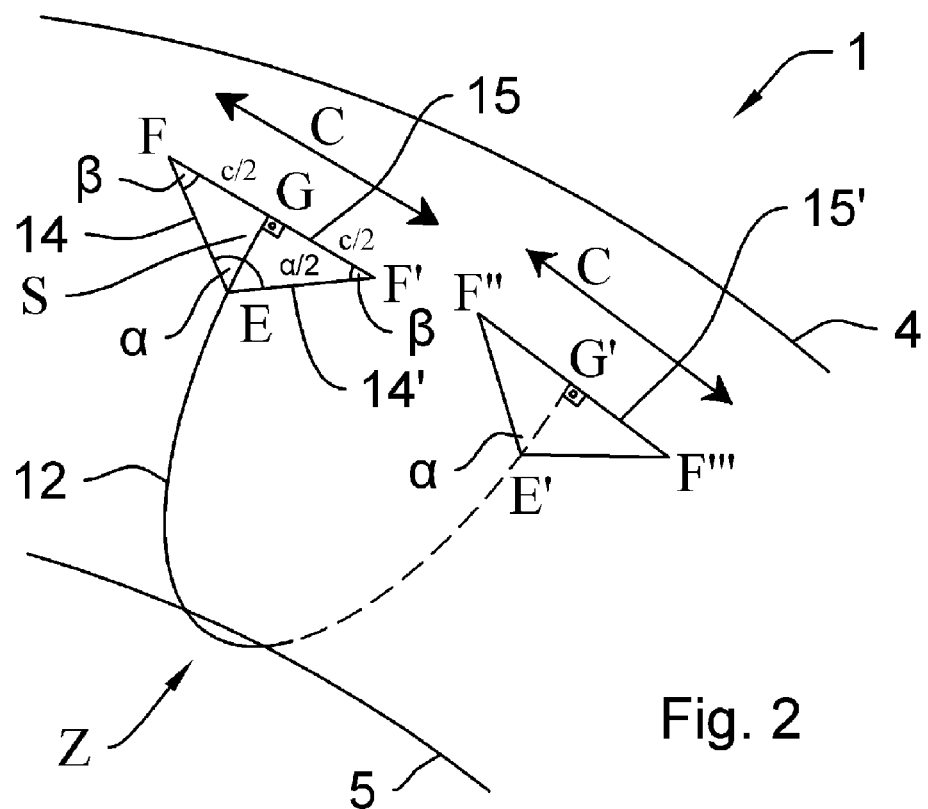
FIG. 2 is a representation of location details for the incisions as per the methods of the invention.

Said device (21) comprises (a few references shown on FIGS. 1 and 2 are made):

a. two longer rules (22) and (23) linked together by a junction (26) and adjustable between them along a hypothetical plan containing them, having rotation and/or translation between one and the other;

b. a flexible measurement element (24) connected to said junction (26) of the two longer rules (22) and (23);

c. two shorter rules (28), (29), each one respectively fixed (32) to one of said longer rules (22), (23), perpendicularly to them, which are able to move in translation along their lengths.

d. optionally, elements (40) to non-permanently clamp the device to the penis or to portions of it, e.g. clamps or staples.

In the illustration of a particular embodiment of the device (21) of the invention as per FIG. 6, the longer rules (22), (23) are provided with trails (20), (31) allowing the translation movement of one with relation to the other one. The longer rules permit the determination e.g. of the central penis axis (6) and the tangential lines (7') and (8'), while trail openings can be used to guide and allow to draw said lines.

Shorter rules (28), (29) are used in the determination of perpendicular lines (10) and (11). They move in this case along said trails (20), (31) of the longer rules (22), (23), keeping position perpendicular to them.

The measurement element (24) is also provided with a trail or tear (35) which is used by the surgeon to determine the bisectrix line (9) guiding the main incision line (12). Being flexible, e.g. as a flexible plastic ribbon, it can surround the body of the penis, facilitating the drafting of line (12). It is provided with an (X) wide tear to allow the drawing of line (12).

The measurement element (24) has rotation movement with relation to the longer rules (22), (23) by means of a clamping (26) also joining it to them. Said clamping means are provided with two concentric axes (26) and. (27), one linked to one of the longer rules (22), (23) and another one linked to the measurement element (24), provided with measurement marks (not shown) allowing the verification of the angles, e.g. when the measurement element is located over the mean angle position, i.e. over the bisectrix (9) between the longer rules (22), (23).

It should be clear that, despite particular embodiments of the invention having been described with regard to a penis having ventral curvature as shown by FIG. 1, the methods of the invention, eventually conjugated with the auxiliary device as described, may be employed to correct curvatures of any kind, i.e. lateral, dorsal, ventral curvatures, besides the conjugation of two simultaneous curvatures, e.g. above and lateral, and also when there is more than one curvature on the same penis.

It should be recognized that, although the invention was described with relation to a few particular embodiments, the person skilled in the art is able to develop a wide variation of equivalent structural or operational details, expanding the above shown methods and device for other purposes, but not deviating from the scope of the invention. Attached claims should be interpreted as covering all equivalents falling within the scope and character of the invention.

What is claimed as being new and desired to be protected by Letters Patent of the United States is as follows:

1. A penis curvature correcting device for correcting the curvature of a penis, said device comprising:
   at least two first rules linked together by a junction and adjustable therebetween along a hypothetical plane containing said first rules, having rotation and translation between said first rules;
   a flexible measurement element connected to said junction of said first rules; and
   at least two second rules each of which being respectively fixed to one of said first rules, perpendicularly to said first rules, said second rules being able to move in translation along said first rules lengths respectively;
   wherein said first rules defining an opening adapted to allow drawing of a central penis axis and tangential lines on a penis;
   wherein said second rules are used in a determination of perpendicular lines on the penis.

2. The penis curvature correcting device according to claim 1 further comprising an attaching element adapted to non-permanently clamping said penis curvature correcting device to the penis or to portions thereof.

3. The penis curvature correcting device according to claim 1, wherein said first rules are provided with rails defined by said opening allowing to move one of said first rules with relation to the other said first rules.

4. The penis curvature correcting device according to claim 1, wherein said second rules are flexible.

5. The penis curvature correcting device according to claim 1, wherein said measurement element is provided with a trail that surrounds said penis adapted to facilitate drafting of an incision line on said penis.

6. The penis curvature correcting device according to claim 5, wherein said tear has a width between 1 mm and 5 mm.

7. The penis curvature correcting device according to claim 1, wherein said first rules are clamped with two concentric axes marked so to allow the visualization and/or verification of an angle, wherein one of said concentric axes being linked to one of said first rules, and the other of said concentric axes being linked to said measurement element with the other of said first rules being clamped by said concentric axes received through said opening of the other of said first rules.

8. The penis curvature correcting device according to claim 1 further comprising at least two concentric axes rotatable in relation to each other, one of said concentric axes being linked to one of said first rules, and the other of said concentric axes being linked to said measurement element.

9. The penis curvature correcting device according to claim 1, wherein said measurement element is flexible and rotatable around a pin, orthogonal to the plane containing said first rules.

10. The penis curvature correcting device according to claim 2, wherein said attaching element is selected from the group consisting of clamps, and staples.

11. The penis curvature correcting device according to claim 1, wherein said penis curvature correcting device is disposable.

12. The penis curvature correcting device according to claim 1, wherein said first rules are provided with a clamping element allowing to non-permanently clamp the position of one of said first rules with relation to the other of said first rules.

13. A penis curvature correcting device comprising:
   at least two first rules linked together by a junction and adjustable therebetween along a hypothetical plan containing said first rules, having rotation and translation between said first rules, said first rules being provided with rails defined by an opening allowing to move one of said first rules with relation to the other said first rules;
   a flexible measurement element connected to said junction of said first rules, said measuring element being provided with a trail that surrounds said penis adapted to facilitate drafting of an incision line on said penis;
   at least two second rules each of which being respectively fixed to one of said first rules, perpendicularly to said first rules, which are able to move in translation along said first rules lengths respectively;
   an attachment element adapted to non-permanently clamping said penis curvature correcting device to the penis or to portions thereof; and
   at least two concentric axes rotatable in relation to each other, one of said concentric axes being linked to one of said first rules, and the other of said concentric axes being linked to said measurement element;
   wherein said opening of said first rules being adapted to allow drawing of a central penis axis and tangential lines on a penis;
   wherein said second rules are used in a determination of perpendicular lines on the penis.

14. The penis curvature correcting device according to claim 13, wherein said first rules are clamped together by way of said two concentric axes which are marked so to allow the visualization and/or verification of an angle between said first rules, wherein one of said concentric axes being linked to one of said first rules, and the other of said concentric axes being linked to said measurement element with the other of said first rules being clamped by said concentric axes received through said opening of the other of said first rules.

15. The penis curvature correcting device according to claim 14, wherein said measurement element is flexible and rotatable around a pin, orthogonal to the plan containing said first rules.

16. The penis curvature correcting device according to claim 15, wherein said attaching element is selected from the group consisting of clamps, and staples.

17. A penis curvature correcting system for correcting the curvature of a penis, said system comprising:
   at least two penis curvature correcting devices each comprising:
      at least two first rules linked together by a junction and adjustable therebetween along a hypothetical plane containing said first rules, having rotation and translation between said first rules, said first rules each defining an opening adapted to allow drawing of a central penis axis and tangential lines on a penis;
      a flexible measurement element connected to said junction of said first rules; and
      at least two second rules each of which being respectively fixed to one of said first rules, perpendicularly to said first rules, said second rules being adapted to move in translation along said first rules lengths respectively, said second rules are used in a determination of perpendicular lines on the penis;
   wherein said two penis curvature correcting devices being attached to the penis parallel with each other.

18. The penis curvature correcting system according to claim 17, wherein each of said first rules are provided with rails defined by said opening allowing to move one of said first rules with relation to the other said first rules respectively; and wherein said measurement element is provided with a trail that surrounds said penis adapted to facilitate drafting of an incision line on said penis.

19. The penis curvature correcting system according to claim 17, wherein each of said penis curvature correcting devices further comprising at least two concentric axes rotatable in relation to each other, one of said concentric axes being linked to one of said first rules, and the other of said concentric axes being linked to said measurement element.

* * * * *